United States Patent [19]

Grolig et al.

[11] 3,949,007

[45] Apr. 6, 1976

[54] PROCESS FOR THE PRODUCTION OF PRIMARY ALKENOLS

[75] Inventors: Johann Grolig; Gerhard Scharfe, both of Leverkusen; Wolfgang Swodenk, Odenthal-Globusch, all of Germany

[73] Assignee: Bayer Aktiengesellschaft, Leverkusen, Germany

[22] Filed: July 12, 1973

[21] Appl. No.: 378,726

Related U.S. Application Data

[63] Continuation of Ser. No. 59,356, July 29, 1970, abandoned.

[30] Foreign Application Priority Data

Aug. 1, 1969 Germany.............................. 1939142

[52] U.S. Cl. ........................ 260/635 R; 260/638 R
[51] Int. Cl.² ....................................... C07C 29/00
[58] Field of Search ..................... 260/635 R, 638 R

[56] References Cited
UNITED STATES PATENTS

| | | | |
|---|---|---|---|
| 2,578,647 | 12/1951 | Stiteler et al.................... | 260/635 R |
| 2,776,323 | 1/1957 | Toland et al.................... | 260/635 R |
| 3,069,475 | 12/1962 | Sidi................................. | 260/635 R |
| 3,098,093 | 7/1963 | Hagemeyer et al............. | 260/638 R |

OTHER PUBLICATIONS

Turoxa et al., "Russian Chemical Reviews", (1965), pp. 161–172.
Wagner et al., "Synthetic Organic Chemistry", (1953), pp. 486–487.

*Primary Examiner*—Joseph E. Evans
*Attorney, Agent, or Firm*—Burgess, Dinklage & Sprung

[57] ABSTRACT

Primary alkenols are produced by transesterifying a primary alkenol acetate with methanol in the presence of the hydroxide or alkoxide of a metal in the first to third main group of the Periodic Table as catalyst. Preferably the methanol is present in large excess and the by-product methyl acetate is removed as an azeotrope with the excess methanol. The reaction is preferably effected under anhydrous conditions and it is substantially quantitative.

8 Claims, No Drawings

PROCESS FOR THE PRODUCTION OF PRIMARY ALKENOLS

This is a continuation of application Serial No. 59,356 filed July 29, 1970, now abandoned.

The present invention is concerned with an economic process for the production of primary alkenols.

It has been found that primary alkenols can be produced in an economically advantageous manner by reacting primary alkenyl acetates with methanol in liquid phase at temperatures between about 0° to 150°C. in the presence of one or more catalysts comprising the hydroxides or alkoxides of a metal of the first to third main group of the Periodic Table.

The conversion of the alkenyl acetates to the primary alkenols can be effected almost completely by carrying out the reaction with an excess of methanol, removing the methyl acetate formed by the reaction by distillation from the equilibrium mass, and separating the excess methanol by distillation. After re-distillation of the residue, primary alkenols are obtained which are substantially colorless and free from metal compounds.

Suitable starting materials for the production of primary alkenols preferably comprise the acetates of mono- or poly- hydroxy unsaturated aliphatic hydrocarbons which contain up to about 18 carbon atoms, such as allyl acetate, methallyl acetate, 1-acetoxy-2-pentene, 1-acetoxy-2-methyl-2-butene, 1-acetoxy-3-methyl-2-butene, 1-acetoxy-2-methylene-butane, 1-acetoxy-2-hexene, 1-acetoxy-2-methyl-2-pentene, 1-acetoxy-3-methyl-2-pentene, 1-acetoxy-4-methyl-2-pentene, 1-acetoxy-2,3-dimethyl-2-butene, 1-acetoxy-2-methylene-pentane, 1-acetoxy-2-heptene, 1-acetoxy-2-methyl-2-hexene, 1-acetoxy-3-methyl-2-hexene, 1-acetoxy-4-methyl-2-hexene, 1-acetoxy-5-methyl-2-hexene, 1-acetoxy-2-ethyl-2-pentene, 1-acetoxy-3-ethyl-2-pentene, 1-acetoxy-2,3-dimethyl-2-pentene, 1-acetoxy-3,4-dimethyl-2-pentene, 1-acetoxy-2-methylene-hexane, 1-acetoxy-2-octene, 1-acetoxy-2-methylene-heptene, 1-acetoxy-2-methylene-4-methyl-hexane, 1-acetoxy-2-methylene-4,4-dimethyl-pentane, 1-acetoxy-2-methylene-4,4-dimethyl-heptane, 1-acetoxy-2-methylene-4,4,6,6-tetra methylheptane, 1,3-diacetoxy-2-methylene-propane, and the like. By means of the reaction, the corresponding primary alkenols are obtained, such as allyl alcohol, methallyl alcohol, 2-pentene-1-ol, 2-methyl-2-butene-1-ol, 3-methyl-2-butene-1-ol, 2-methylene-1-butanol, 2-hexene-1-ol, 2-methyl-2-pentene-1-ol, 3-methyl-2-pentene-1-ol, 4-methyl-2-pentene-1-ol, 2,3-dimethyl-2-butene-1-ol, 2-methylene-1-pentanol, 2-heptene-1-ol, 2-methyl-2-hexene-1-ol, 3-methyl-2-hexene-1-ol, 4-methyl-2-hexene-1-ol, 5-methyl-2-hexene-1-ol, 2-ethyl-2-pentene-1-ol, 3-ethyl-2-pentene-1-ol, 2,3-dimethyl-2-pentene-1-ol, 3,4-dimethyl-2-pentene-1-ol, 2-methylene-1-hexanol, 2-octene-1-ol, 2-methylene-1-heptanol, 2-methylene-4-methyl-1-hexanol, 2-methylene-4,4-dimethyl-1-pentanol, 2-methylene-4,4-dimethyl-1-heptanol, 2-methylene-4,4,6,6-tetramethyl-1-heptanol, 2-methylene-1,3-propane diol, and the like.

The methyl acetate formed in the reaction can be separated as an azeotrope with methanol by distillation from the excess methanol. In known manner by hydrolysis with acid catalysts the methyl acetate can be split into methanol and acetic acid. From the hydrolysis reaction mixture, the methanol can be recovered in known manner and can be returned for the conversion of the primary alkenyl acetates to alkenols. The acetic acid formed by the hydrolysis of the methyl acetate can be employed in pure form or as aqueous acetic acid for different chemical purposes. By way of example, the acetic acid can be recycled to form alkenyl acetates by reaction with the corresponding olefin and oxygen. In this manner only olefin and oxygen are required stoichiometrically for the production of the primary alkenols, i.e. the production of the primary alkenols effectively proceeds in accordance with the equation:

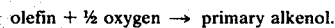

olefin + ½ oxygen → primary alkenol.

The reaction of the alkenyl acetates with methanol is advantageously carried out under substantially anhydrous conditions. The catalysts which are claimed can be obtained in various ways. As described by Meerwein and Bresin in Annalen 476, pages 113–150, alkoxides can be produced by dissolving one or more of the metals of the first to third main group of the Periodic Table in alcohols, e.g. alkali metal hydroxides such as potassium hydroxide or sodium hydroxide can be dissolved in methanol or other lower alkanol. Complex alcoholates can be produced by dissolving the corresponding metals in alcohols such as lower alkanols in stoichiometric ratio or simply by combining stoichiometric quantities of two simple alkoxides.

The following catalyst, amongst others, are suitable for use in the practice of the invention: lithium hydroxide, potassium hydroxide, sodium hydroxide, lithium methylate, lithium methoxide sodium methylate, potassium methylate, magnesium methylate, calcium methylate, aluminum methylate, and the like, as well as complex alkoxide salts such as lithium-magnesium methylate, lithium-calcium methylate, lithium-boron methylate, lithium-aluminum methylate, sodium-magnesium methylate, sodium-calcium methylate, sodium-boron methylate, sodium-aluminum methylate, potassium-magnesium methylate, potassium-calcium methylate, potassium-boron methylate, potassium-aluminum methylate, calcium-boron methylate, calcium-aluminum methylate, magnesium-boron methylate, magnesium-aluminum methylate, and the like.

The catalysts are dissolved or suspended in the ester to the extent of about 0.1 to 10% by weight of the methanol. The catalysts can be separated out mechanically after the reaction, provided they are insoluble at room temperature, and be used again for a new reaction, or they are recovered as distillation residue after redistillation of the alkenol and returned as such for reuse. If desired, it is possible to dispense entirely with the recovery of the inexpensive catalyst. The relative proportions of the organic components can be varied within wide limits. It is, however, advantageous to use the methanol in molar excess, in order quantitatively to convert the alkenyl acetate, e.g. about 2 to 25 and preferably about 3 to 20 times the stoichiometric quantity.

The reaction can take place intermittently or continuously. The intermittent reaction is preferably conducted by initially placing the alkenyl acetate, methanol and the catalyst in a reaction vessel and heating the reaction mixture to reflux temperature. By means of a distillation column, methyl acetate is constantly distilled off proportionately with the progress of the reaction until the introduced alkenyl acetate is completely reacted. The separation of the alkenol thus obtained is effected, after distilling off the excess methanol which has not reacted, by simple redistillation, possibly after previously separating out any undissolved catalyst fractions. The catalyst, which is present as the residue of filtration or distillation, is used again in another reaction cycle.

When the process is carried out intermittently or continuously, it is also possible to work in such a way that initially the alkenyl ester is caused to react with the methanol and the catalyst in a reaction vessel from which a mixture of methanol and methyl acetate is distilled off, and in a second stage or in additional stages the mixture of formed alkenol and unreacted alkenyl acetate, which mixture is free from methanol and methyl acetate, is reacted with methanol and catalyst. In many cases, it is possible, and here in a two-stage process, to obtain an alkenol which is practically free from alkenyl acetate. From the mixture of methanol and methyl acetate which is obtained by this procedure, the methyl acetate can be separated in known manner by distillation.

When the reaction is conducted continuously, a solution of the catalyst in the mixture of alkenyl acetate and methanol can, for example, be introduced into a distillation column, and the azeotrope of methyl acetate and methanol can be continuously distilled off at the top of this column. The residue from this first column can then be freed in a second distillation column from methanol, and it is possible to obtain a residue which, after redistillation, consists of pure primary alkenol.

The invention will be further illustrated in the following examples wherein all parts are by weight unless otherwise specified.

EXAMPLE 1

300 g of allyl acetate (3 mols), 1600 g of methanol (50 mols) and 3 g of anhydrous KOH were placed in a 4-liter three-neck spherical flask with a stirrer mechanism and attached distillation column and heated under reflux for 1 hour while stirring. A temperature of 54°C. was adjusted at the top of the column and of 55.5°C. at the bottom thereof. Analysis of the flask contents showed that 95% of the introduced allyl acetate had been trans-esterified into allyl alcohol. Methyl acetate, as an azeotrope with methanol, was now distilled off in 4½ hours in the boiling range from 54°C. (azeotrope boiling point) to 65°C. (pure methanol), the trans-esterification of the allyl acetate being completed. No allyl acetate could be detected by gas chromotography in the distillation residue.

After distilling off the excess methanol and re-distillation of the residue containing the catalyst, 170 g of allyl alcohol of b.p. 97°C. were obtained. Total yield: 98%. Purity: 99.9% (remainder methanol).

EXAMPLE 2

The trans-esterification of allyl acetate with methanol to allyl alcohol and methyl acetate was carried out continuously in a packed distillation column of a length of 2 meters and an internal diameter of 30 mm.

A mixture of 65 g of allyl acetate, 62.4 g of methanol and 0.65 g of KOH was pumped per hour into the middle of the column. The molar ratio of methanol to allyl acetate was 3:1. At the top, an azeotropic mixture of methyl acetate and methanol of b.p. 54°C. was taken off, while at the bottom a mixture of allyl alcohol, excess methanol and catalyst was removed, which contained only traces of allyl acetate. This residue was continuously pumped into another distillation column and separated into a head product (b.p. 65°C.) consisting substantially of methanol and a residue containing only allyl alcohol, apart from catalyst. The re-distillation of this allyl alcohol residue yielded pure allyl alcohol of b.p. 97°C. and purity of more than 99.9%.

EXAMPLE 3

114 g of methallyl acetate (1 mol) and 160 g of methanol (5 mols) were allowed to react in the presence of 2.2 g of KOH (2% by weight of the ester) for 30 minutes at room temperature. Analysis showed 1.73% of the total mixture to be unreacted methallyl acetate, corresponding to a conversion of 96 mol %. Upon distilling off the methanol-methyl acetate azeotrope, all the methyl acetate was converted to methallyl alcohol. Working up by distillation yielded pure methallyl alcohol of b.p. 114°C. and a purity of 99.56%.

EXAMPLE 4

68 g of methallyl acetate (0.6 mol) and 192 g of methanol (6 mols) were allowed to react in the presence of 2 g of KOH for 30 minutes at room temperature. Analysis thereafter showed a residual content of unreacted methallyl acetate of 0.53% by weight; this corresponds to a conversion of 98 mol %. By distilling off the methanol-methyl acetate azeotrope, the conversion was quantitative and, after working up by distillation, pure methallyl alcohol was obtained.

EXAMPLE 5

43 g of 1,3-diacetoxy-2-methylenepropane (0.25 mol) and 160 g of methanol (5 mols) were mixed with 1.7 g of KOH and allowed to react for 30 minutes at room temperature. Methyl acetate was then distilled off with methanol (b.p. 54–55°C.) and thereby the reaction was completed. After distilling off the excess methanol, the 2-methylene-1,3-propanediol was left as residue together with the catalyst. By vacuum distillation with a rotary thin-film evaporator, catalyst-free diol could be obtained therefrom.

EXAMPLE 6

85 g of 1-acetoxy-2-methylene-4,4-dimethylpentane ("acetoxy-isooctene"; 0.5 mol), 122 g of methanol (3.5 mols) and 1.1 g of KOH were stirred for 30 minutes at room temperature. Analysis showed 1.27% by weight of unreacted acetoxyisooctene, corresponding to a conversion of 97 mol %. After distilling off methyl acetate and methanol to a pot temperature of 178°C., the residue had the following composition:

| Component | % by weight |
|---|---|
| 2-methylene-4,4-dimethyl-1-pentanol | 95.00 |
| acetoxyisooctene | 0.12 |
| methanol and light-boiling substances | 4.88 |
| | 100.00 |

Fractionation provided a colorless distillate of b.p. 85°C./20 mm. Hg with a content of 2-methylene-4,4-dimethyl-1-pentanol of 99.63% by weight.

EXAMPLE 7

100 g of acetoxyisooctene, 100 g of methanol and 1 g of NaOH were stirred at room temperature and analyzed at short time intervals. The content of unreacted acetoxyisooctene in dependence on time is shown by the following table:

| Time (hours) | Acetoxyisooctene % by weight |
|---|---|
| 0.5 | 2.19 |
| 1 | 2.15 |
| 2 | 2.13 |

The reaction was therefore substantially at equilibrium conversion of 96 mol % after 30 minutes. Methyl acetate and methanol were then distilled off in 2 hours. 100 g of methanol were once again added to the distillation residue and, for completing the reaction, methanol and also a small quantity of methyl acetate were quickly distilled off.

| Component | % by weight |
|---|---|
| 2-methylene-4,4-dimethyl-1-pentanol | 95.81 |
| acetoxyisooctene | 0.28 |
| methanol and traces of light-boiling substances | 3.91 |
| | 100.00 |

Distillation by fractionation supplied, at 20 mm. Hg, a colorless distillate of b.p. 84–°85°C. and a content of 99.50% by weight of 2-methylene-4,4-dimethyl-1-pentanol.

EXAMPLE 8

The reaction of acetoxyisooctene with methanol to form 2-methylene-4,4-dimethyl-1-pentanol was carried out with various alkoxides and complex salts of alkoxides. The quantites used were as follows:

| | |
|---|---|
| acetoxyisooctene | 51 g |
| methanol | 160 g |
| catalyst | 5 g (2.3% by weight). |

The reaction mixture was heated to reflux while stirring and the methanol-methyl acetate azeotrope was constantly distilled off. The conversion to 2-methylene-4,4-dimethyl-1-pentanol was established by analysis of the methyl acetatefree distillation residue. The results are shown in the following table:

| Catalyst | Distillation time, hours | Conversion, Mol % |
|---|---|---|
| Li OCH$_3$ | 4.6 | 99.2 |
| Na OCH$_3$ | 4.6 | 98.6 |
| Mg (OCH$_3$)$_2$ | 6.8 | 99.6 |
| Ca (OCH$_3$)$_2$ | 4.6 | 100.0 |
| Li$_2$Mg (OCH$_3$)$_4$ | 4.0 | 99.8 |
| Li$_2$Ca (OCH$_3$)$_4$ | 8.8 | 99.4 |
| Li B (OCH$_3$)$_4$ | 7.3 | 98.8 |
| Li Al (OCH$_3$)$_4$ | 3.7 | 99.0 |
| Na$_2$Mg (OCH$_3$)$_4$ | 6.5 | 98.3 |
| Na$_2$ Ca (OCH$_3$)$_4$ | 5.8 | 99.7 |
| Na B (OCH$_3$)$_4$ | 6.2 | 100.0 |
| Na Al (OCH$_3$)$_4$ | 6.5 | 99.7 |
| K$_2$ Mg (OCH$_3$)$_4$ | 4.0 | 98.1 |
| K B (OCH$_3$)$_4$ | 4.2 | 99.7 |
| K Al (OCH$_3$)$_4$ | 7.6 | 99.7 |
| Mg [B (OCH$_3$)$_4$]$_2$ | 6.0 | 99.3 |
| Ca [B (OCH$_3$)$_4$]$_2$ | 8.5 | 100.0 |
| Ca [Al (OCH$_3$)$_4$]$_2$ | 7.8 | 100.0 |

It will be appreciated that the instant specification and examples are set forth by way of illustration and not limitation, and that various modifications and changes may be made without departing from the spirit and scope of the present invention.

What is claimed is:

1. The process for the production of a primary alkenol or an alpha, omega-alkenediol which comprises contacting a primary alkenol or an alpha, omega -alkenediol acetate with about 2 to 25 times the stoichiometric amount of methanol at a temperature ranging between about 0° and 150°C. in the presence of one or more hydroxides or alkoxides of a metal of the first to third main groups of the Periodic Table or stoichiometric mixtures of two of said alkoxides as catalyst, distilling off the methyl acetate formed in the reaction as an azeotrope with methanol, adding methanol to the residue and distilling off said added methanol, thereby to complete the conversion of said primary alkenol or alkenediol acetate to said primary alkenol or alkenediol, and subjecting the distillation residue to a vacuum distillation to distill off the primary alkenol or alkendiol and leave behind the catalyst which is recycled.

2. The process according to claim 1 wherein the stoichiometric mixture of two of said alkoxides is produced by dissolving the corresponding metals in alkanols.

3. The process according to claim 1, wherein said reaction is effected under substantially anhydrous conditions.

4. The process according to claim 2, wherein said catalyst is at least one methoxide of a metal selected from the group consisting of lithium, sodium, magnesium, calcium, aluminum and potassium.

5. The process according to claim 1 wherein the material contacted is an alpha, omega-alkenediol acetate and the catalyst is a methoxide.

6. The process of claim 1 wherein said catalyst is selected from the group consisting of an alkoxide of lithium, sodium, potassium, calcium, magnesium, aluminum, lithium-magnesium, lithium-calcium, lithium-boron, lithium-aluminum, sodium-magnesium, sodium-calcium, sodium-boron, sodium-aluminum, potassium-magnesium, potassium-calcium, potassium-boron, potassium-aluminium, calcium-boron, calcium-aluminum, magnesium-boron and magnesium-aluminum.

7. The process of claim 1 wherein said catalyst is an alkali metal hydroxide or alkoxide.

8. The process of claim 1 wherein said catalyst is potassium hydroxide.

* * * * *